(12) United States Patent
Hubschwerlen et al.

(10) Patent No.: US 7,557,214 B2
(45) Date of Patent: Jul. 7, 2009

(54) INTERMEDIATE PRODUCTS FOR PRODUCING OXAZOLIDINONE-QUINOLONE HYBRIDS

(75) Inventors: Christian Hubschwerlen, Durmenach (FR); Jean-Luc Specklin, Kembs-Schaeferhof (FR); Jean Phillippe Surivet, Saint-Louis (FR); Daniel Baeschlin, Arlesheim (CH)

(73) Assignee: Morphochem Aktiengesellschaft für Kombinatorische Chemie, Munich (DE)

( * ) Notice: Subject to any disclaimer, the term of this patent is extended or adjusted under 35 U.S.C. 154(b) by 83 days.

(21) Appl. No.: 10/570,775

(22) PCT Filed: Sep. 3, 2004

(86) PCT No.: PCT/EP2004/009858

§ 371 (c)(1),
(2), (4) Date: Mar. 3, 2006

(87) PCT Pub. No.: WO2005/023801

PCT Pub. Date: Mar. 17, 2005

(65) Prior Publication Data

US 2007/0004769 A1  Jan. 4, 2007

(30) Foreign Application Priority Data

Sep. 3, 2003  (DE) ............................... 103 40 485

(51) Int. Cl.
*C07D 211/00* (2006.01)
*C07D 211/26* (2006.01)

(52) U.S. Cl. ....................... 546/209; 548/229

(58) Field of Classification Search ............... 546/156, 546/209, 113, 229; 548/229; 544/370; 540/604
See application file for complete search history.

(56) References Cited

U.S. PATENT DOCUMENTS

2004/0132764 A1* 7/2004 Locher ...................... 514/300

FOREIGN PATENT DOCUMENTS

| WO | WO-00/10566 | | 3/2000 |
|---|---|---|---|
| WO | 2001/09107 | * | 2/2001 |
| WO | WO-01/09107 A1 | | 2/2001 |
| WO | 2001/46164 | * | 6/2001 |
| WO | WO-01/46164 A1 | | 6/2001 |
| WO | WO-03/032962 A2 | | 4/2003 |
| WO | WO-2004/069816 A1 | | 8/2004 |
| WO | 2004/096221 | * | 11/2004 |

OTHER PUBLICATIONS

Hcaplus 138:338143.*
Hcaplus 138:304289.*
Hcaplus 138:304288.*
Hubschwerlen et. al., Structure-Activity Relationship in the Oxazolidinone-Quinolone Hybrid Series: Influence of the Central Spacer on the Antibacterial Activity and the Mode of Action, Bioorganic & Medicinal Chemistry Letters, (2003), pp. 4229-4233.*
Hcaplus 141:395540.*
Selvakumar et. al, Influence of Ethylene-Oxy Spacer Group on the Activity of Linezolid: Synthesis of Potent Antiberials Possessing a Thiocarbonyl Group, Bioorganic & Medicinal Chemistry Letters, 13 (2003) 4169-4172, Aug. 2003.*
Hcaplus 141:207195, A preparation of (oxazolidinylmethyl)acetamide derivatives, useful as antimicrobial agents, Aug. 19, 2004, Mehta et. al.*

* cited by examiner

*Primary Examiner*—Janet L. Andres
*Assistant Examiner*—Binta Robinson
(74) *Attorney, Agent, or Firm*—Peter F. Corless; Nicholas J. DiCeglie; Edwards Angell Palmer & Dodge LLP

(57) ABSTRACT

The present invention describes intermediates (ZP) for a novel and efficient synthesis of compounds in which the pharmacophores of quinolone and oxazolidinone are linked to one another by way of a chemically stable linker.

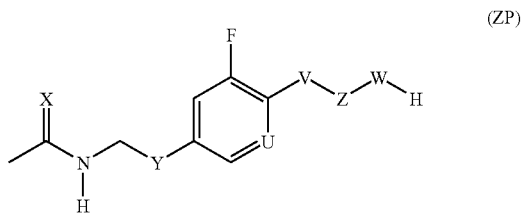

8 Claims, No Drawings

INTERMEDIATE PRODUCTS FOR PRODUCING OXAZOLIDINONE-QUINOLONE HYBRIDS

The present invention describes intermediates (ZP) for a novel and efficient synthesis of end products in which the pharmacophores of quinolone and oxazolidinone are linked to one another by way of a chemically stable linker. End products of that kind are described in WO 03032962 and are distinguished by a high level of activity against human and animal bacteria. The present invention relates also to a novel and efficient synthesis of those intermediates as well as to the end products.

The present invention relates to compounds of formula (ZP)

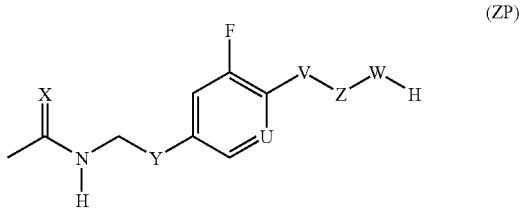

wherein
U is a nitrogen atom or a CH group;
V is an oxygen atom, a sulphur atom or a group of formula $CR^6R^7$;
W is a bond, an oxygen atom, a sulphur atom, a group of formula $NR^8$, or an optionally substituted cycloalkylene, heterocycloalkylene, alkylcycloalkylene, heteroalkylcycloalkylene, arylene, heteroarylene, aralkylene or heteroaralkylene group;
X is an oxygen atom or a sulphur atom;
Y is selected from the following groups:

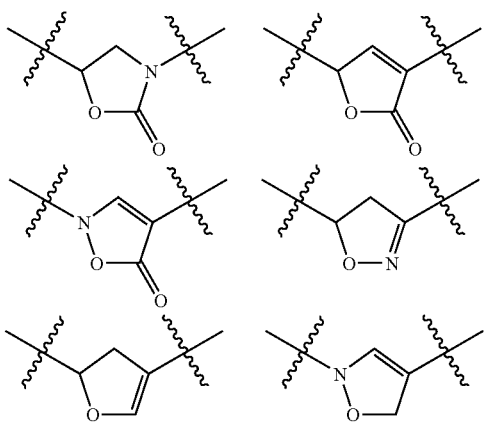

z is an optionally substituted alkylene, alkenylene, alkynylene, heteroalkylene, cycloalkylene, heterocycloalkylene, alkylcycloalkylene, heteroalkylcycloalkylene, arylene, heteroarylene, aralkylene or heteroaralkylene group;
the radicals $R^6$ and $R^7$ are each independently of the other a hydrogen atom, a halogen atom, a hydroxy, amino, nitro or thiol group, an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or a heteroaralkyl radical;

$R^8$ is a hydrogen atom, an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or a heteroaralkyl radical.

The term alkyl refers to a saturated, straight-chain or branched hydrocarbon group that contains from 1 to 20 carbon atoms, preferably from 1 to 12 carbon atoms, especially from 1 to 6 carbon atoms, for example a methyl, ethyl, propyl, isopropyl, n-butyl, isobutyl, tert-butyl, n-pentyl, n-hexyl or 2,2-dimethylbutyl group.

The terms alkenyl and alkynyl refer to at least partially unsaturated, straight-chain or branched hydrocarbon groups that contain from 2 to 20 carbon atoms, preferably from 2 to 12 carbon atoms, especially from 2 to 6 carbon atoms, for example an ethenyl, allyl, acetylenyl, propargyl, isoprenyl or hex-2-enyl group. Preferably, alkenyl groups have one or two (especially one) double bond(s) and alkynyl groups have one or two (especially one) triple bond(s).

Furthermore, the terms alkyl, alkenyl and alkynyl refer to groups in which one or more hydrogen atoms, each independently of any other(s), have been replaced by a halogen atom (preferably F or Cl), such as, for example, a 2,2,2-trichloroethyl or a trifluoromethyl group.

The term heteroalkyl refers to an alkyl, an alkenyl or an alkynyl group (for example heteroalkenyl, heteroalkynyl), in which one or more (preferably 1, 2 or 3) carbon atoms, each independently of any other(s), have been replaced by an oxygen, nitrogen, phosphorus, boron, selenium, silicon or sulphur atom (preferably oxygen, sulphur or nitrogen). The term heteroalkyl furthermore refers to a carboxylic acid or to a group derived from a carboxylic acid such as, for example, acyl, acylalkyl, alkoxycarbonyl, acyloxy, acyloxyalkyl, carboxyalkylamide or alkoxycarbonyloxy.

Examples of heteroalkyl groups are groups of formulae $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, $R^a$ being a hydrogen atom, a $C_1$-$C_6$alkyl, a $C_2$-$C_6$-alkenyl or a $C_2$-$C_6$alkynyl group; $R^b$ being a hydrogen atom, a $C_1$-$C_6$alkyl, a $C_2$-$C_6$alkenyl or a $C_2$-$C_6$alkynyl group; $R^c$ being a hydrogen atom, a $C_1$-$C_6$alkyl, a $C_2$-$C_6$alkenyl or a $C_2$-$C_6$alkynyl group; $R^d$ being a hydrogen atom, a $C_1$-$C_6$alkyl, a $C_2$-$C_6$alkenyl or a $C_2$-$C_6$alkynyl group and $Y^a$ being a direct bond, a $C_1$-$C_6$alkylene, a $C_2$-$C_6$alkenylene or a $C_2$-$C_6$alkynylene group, each heteroalkyl group containing at least one carbon atom and it being possible for one or more hydrogen atoms to have been replaced by fluorine or chlorine atoms. Specific examples of heteroalkyl groups are methoxy, trifluoromethoxy, ethoxy, n-propoxy, isopropoxy, tert-butoxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, enol ether, dimethylaminomethyl, dimethylaminoethyl, acetyl, propionyl, butyryloxy, acetoxy, methoxycarbonyl, ethoxycarbonyl, N-ethyl-N-methylcarbamoyl and N-methylcarbamoyl. Further examples of heteroalkyl groups are nitrile, isonitrile, cyanate, thiocyanate, isocyanate, isothiocyanate and alkylnitrile groups. An example of a heteroalkylene group is a group of formula —CH$_2$CH(OH)—.

The term cycloalkyl refers to a saturated or partially unsaturated cyclic group (e.g. a cyclic group that contains one, two or more double bonds, such as a cycloalkenyl group), containing one or more rings (preferably 1 or 2) that have from 3 to 14 ring carbon atoms, preferably from 3 to 10 (especially 3, 4, 5, 6 or 7) ring carbon atoms. The term cycloalkyl refers furthermore to corresponding groups in which one or more hydrogen atoms, each independently of any other(s), have been replaced by fluorine, chlorine, bromine or iodine atoms or by OH, =O, SH, =S, NH$_2$, =NH or NO$_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetralin, cyclopentylcyclohexyl, fluorocyclohexyl or cyclohex-2-enyl group.

The term heterocycloalkyl refers to a cycloalkyl group as defined above in which one or more (preferably 1, 2 or 3) ring carbon atoms, each independently of any other(s), have been replaced by an oxygen, nitrogen, silicon, selenium, phosphorus or sulphur atom (preferably oxygen, sulphur or nitrogen). A heterocycloalkyl group has preferably 1 or 2 ring(s) containing from 3 to 10 (especially 3, 4, 5, 6 or 7) ring atoms. The term heterocycloalkyl refers furthermore to groups in which one or more hydrogen atoms, each independently of any other(s), have been replaced by fluorine, chlorine, bromine or iodine atoms or by OH, =O, SH, =S, NH$_2$, =NH or NO$_2$ groups. Examples are a piperidyl, piperazinyl, morpholinyl, urotropinyl, pyrrolidinyl, tetrahydrothiophenyl, tetrahydropyranyl, tetrahydrofuryl or 2-pyrazolinyl group and also lactams, lactones, cyclic imides and cyclic anhydrides.

The term alkylcycloalkyl refers to groups containing both cycloalkyl and alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group containing one or two rings systems that have from 3 to 10 (especially 3, 4, 5, 6 or 7) carbon atoms, and one or two alkyl, alkenyl or alkynyl groups having 1 or 2 to 6 carbon atoms.

The term heteroalkylcycloalkyl refers to alkylcycloalkyl groups as defined above in which one or more (preferably 1, 2 or 3) carbon atoms, each independently of any other(s), have been replaced by an oxygen, nitrogen, silicon, selenium, phosphorus or sulphur atom (preferably oxygen, sulphur or nitrogen). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The term aryl or Ar refers to an aromatic group that has one or more rings and contains from 6 to 14 ring carbon atoms, preferably from 6 to 10 (especially 6) ring carbon atoms. The term aryl (or Ar) refers furthermore to groups in which one or more hydrogen atoms, each independently of any other(s), have been replaced by fluorine, chlorine, bromine or iodine atoms or by OH, SH, NH$_2$ or NO$_2$ groups. Examples are a phenyl, naphthyl, biphenyl, 2-fluorophenyl, anilinyl, 3-nitrophenyl or 4-hydroxyphenyl group.

The term heteroaryl refers to an aromatic group that has one or more rings and contains from 5 to 14 ring atoms, preferably from 5 to 10 (especially 5 or 6) ring atoms, and contains one or more (preferably 1, 2, 3 or 4) oxygen, nitrogen, phosphorus or sulphur ring atoms (preferably O, S or N). The term heteroaryl refers furthermore to groups in which one or more hydrogen atoms, each independently of any other(s), have been replaced by fluorine, chlorine, bromine or iodine atoms or by OH, SH, NH$_2$ or NO$_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl groups.

The term aralkyl refers to groups containing both aryl and alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetralin, dihydronaphthalene, indanone, phenylcyclopentyl, cumene, cyclohexylphenyl, fluorene and indan. An aralkyl group preferably contains one or two aromatic ring systems (1 or 2 rings) containing from 6 to 10 carbon atoms and one or two alkyl, alkenyl and/or alkynyl groups containing 1 or 2 to 6 carbon atoms and/or a cycloalkyl group containing 5 or 6 ring carbon atoms.

The term heteroaralkyl refers to an aralkyl group as defined above in which one or more (preferably 1, 2, 3 or 4) carbon atoms, each independently of any other(s), have been replaced by an oxygen, nitrogen, silicon, selenium, phosphorus, boron or sulphur atom (preferably oxygen, sulphur or nitrogen), that is to say to groups containing both aryl or heteroaryl and alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing 5 or 6 to 10 ring carbon atoms and one or two alkyl, alkenyl and/or alkynyl groups containing 1 or 2 to 6 carbon atoms and/or one cycloalkyl group containing 5 or 6 ring carbon atoms, 1, 2, 3 or 4 or those carbon atoms, each independently of any other(s), having been replaced by oxygen, sulphur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are a tetrahydroisoquinolyl-, benzoyl-, 2- or 3-ethylindolyl-, 4-methylpyridino-, 2-, 3- or 4-methoxyphenyl-, 4-ethoxyphenyl-, 2-, 3- or 4-carboxyphenylalkyl group.

The terms alkyl, alkenyl, alkynyl, heteroalkyl, cycloalkyl, heterocycloalkyl, alkylcycloalkyl, heteroalkylcycloalkyl, aryl, heteroaryl, aralkyl and heteroaralkyl refer to groups in which one or more hydrogen atoms of such groups, each independently of any other(s), have been replaced by fluorine, chlorine, bromine or iodine atoms or by OH, =O, SH, =S, $NH_2$, =NH or $NO_2$ groups.

The expression "optionally substituted" refers to groups in which one or more hydrogen atoms, each independently of any other(s), have been replaced by fluorine, chlorine, bromine or iodine atoms or by OH, =O, SH, =S, $NH_2$, =NH or $NO_2$ groups. The expression refers furthermore to groups that are substituted by unsubstituted $C_1$-$C_5$alkyl, $C_2$-$C_6$alkenyl, $C_2$-$C_6$alkynyl, $C_1$-$C_6$heteroalkyl, $C_3$-$C_{10}$cycloalkyl, $C_2$-$C_9$heterocycloalkyl, $C_6$-$C_{10}$aryl, $C_1$-$C_9$-heteroaryl, $C_7$-$C_{12}$aralkyl or $C_2$-$C_{11}$heteroaralkyl groups.

Owing to their substitution, the compounds described in the present Application may contain one or more centres of chirality. The present invention therefore includes both all pure enantiomers and all pure diastereoisomers and also mixtures thereof in any mixing ratio. The present invention moreover also includes all cis/trans-isomers of the compounds of the general formula (I) and also mixtures thereof. The present invention moreover includes all tautomeric forms of the described compounds.

U is preferably a CH group.

In turn, $R^6$ and $R^7$ are preferably hydrogen atoms.

Furthermore, V is preferably an oxygen atom.

In addition, Y has preferably the following formula:

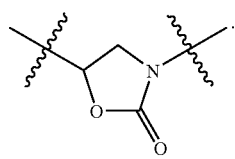

Furthermore, W is preferably an oxygen atom, a sulphur atom, a group of formula $NR^8$, or an optionally substituted heterocycloalkylene, heteroalkylcycloalkylene, heteroarylene or heteroaralkylene group, the H atom bonded to the group W preferably being bonded to an oxygen atom, a sulphur atom or a nitrogen atom.

Furthermore, W is preferably an optionally substituted heterocycloalkylene group containing a ring having 4, 5, 6 or 7 ring atoms; W is especially substituted by an OH group.

In turn, Z is preferably an optionally substituted $C_{1-4}$alkylene group.

Z is especially preferably a $CH_2$ or a $CH_2CH_2$ group.

Furthermore, W is preferably a piperidyl or a pyrrolidinyl group, wherein those groups may optionally be substituted by an OH, $OPO_3H_2$, $OSO_3H$ or a heteroalkyl group carrying at least one OH, $NH_2$, $SO_3H$, $PO_3H_2$ or COOH group (especially an OH group).

Especially preferably, Z-W together are a group of formula:

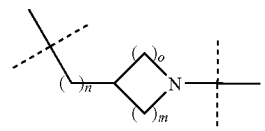

wherein n is 1 or 2, m is 1 or 2 and o is 1 or 2, wherein that group may optionally be substituted by an OH, $OPO_3H_2$, $OSO_3H$ or a heteroalkyl group carrying at least one OH, $NH_2$, $SO_3H$, $PO_3H_2$ or COOH group.

Especially preferably, W has the following structure:

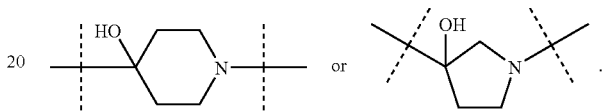

Compounds of formula (ZP) can be used in the synthesis of compounds of formula (I)

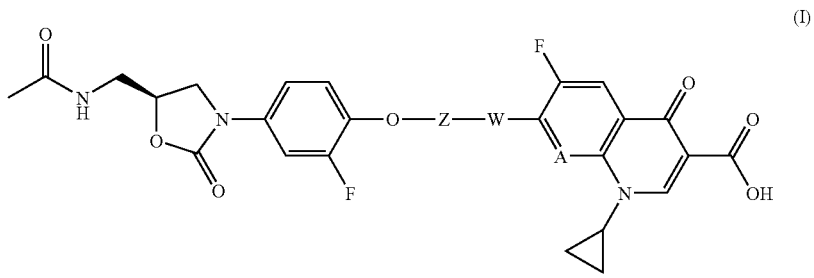

(I)

wherein Z is an optionally substituted $C_{1-4}$alkylene group, A is a nitrogen atom or a CH group and W is an optionally substituted heterocycloalkylene group that contains at least one nitrogen atom and wherein the quinoline radical is bonded to that nitrogen atom.

Compounds of formula (I) can be prepared as follows:

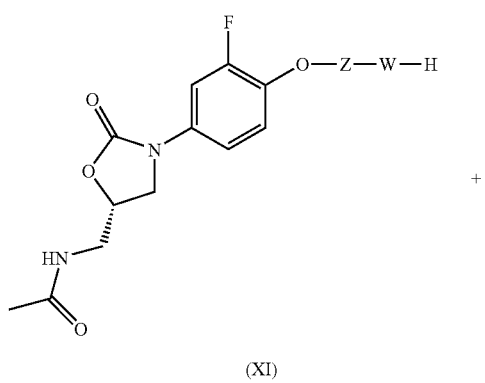

(XI)

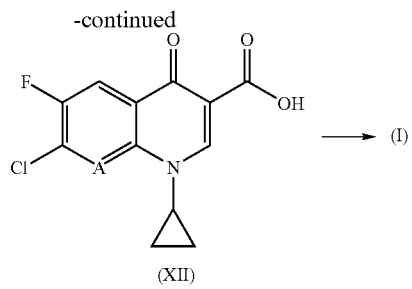

(XII)

wherein compound (XI) is a compound according to the present invention and compound (XII) is preferably used in the form of a boron complex (for example in the form of a boron diacetate complex).

Reaction conditions preferred for that Step are: N-methylpyrrolidone, trimethylsilyl chloride, Hünig Base or K$_2$CO$_3$, 80° C. Compounds according to the invention can be prepared, for example, by the following synthesis route:

Step 1:

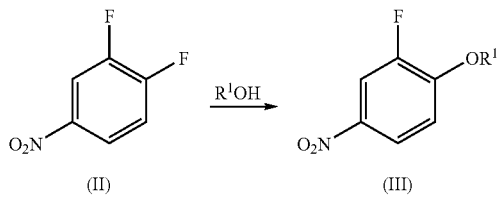

Step 2:

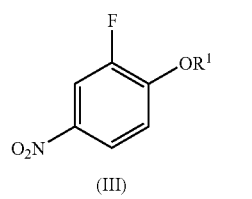

(III)

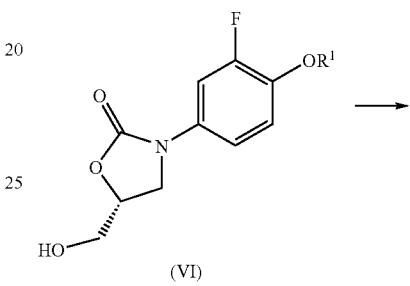

(IV)

Step 3:

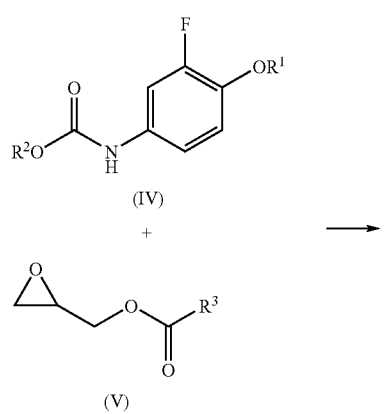

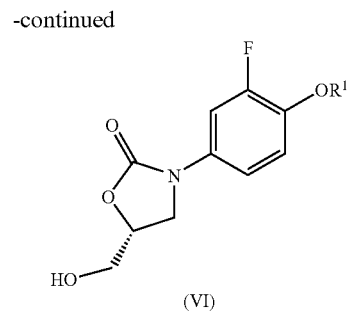

(VI)

Step 4:

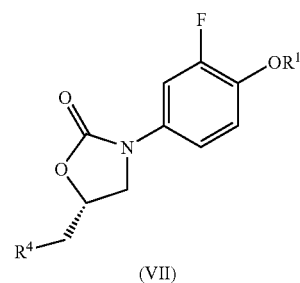

(VI)

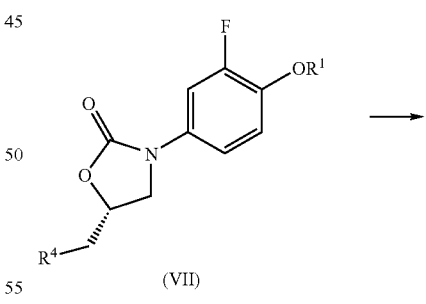

(VII)

Step 5:

(VII)

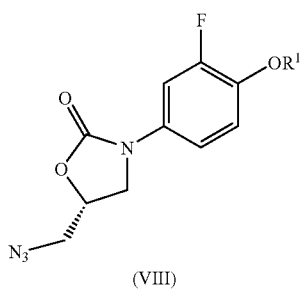

(VIII)

Step 6:
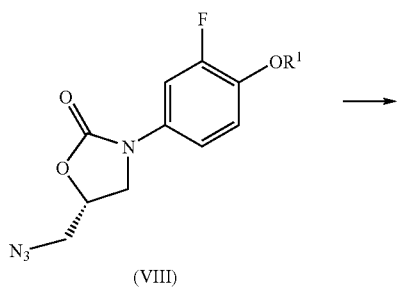
Step 8:
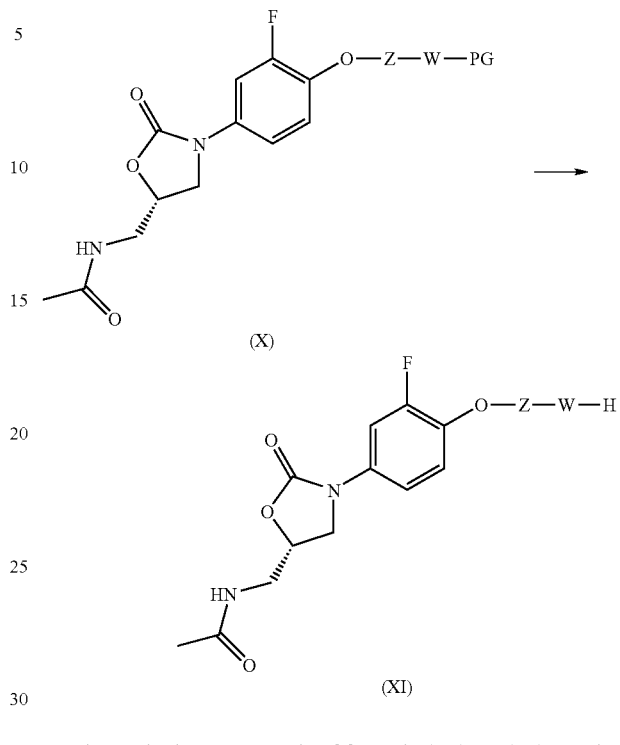
Alternatively, compounds of formula (ZP), or (XI), can be prepared by the following synthesis route:
Step 7:
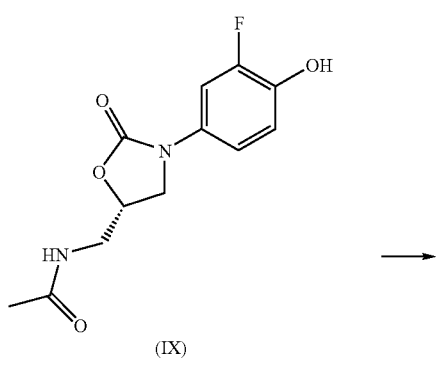
Step 1:
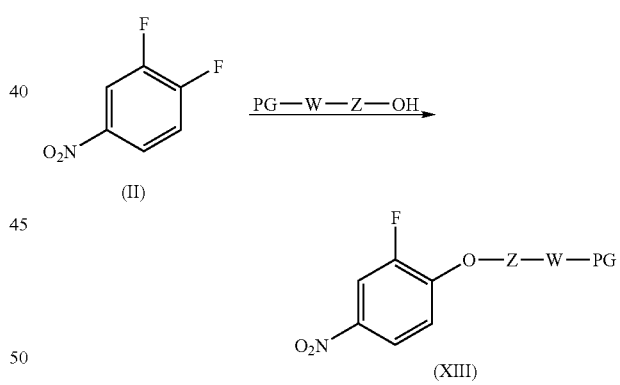
Step 2:
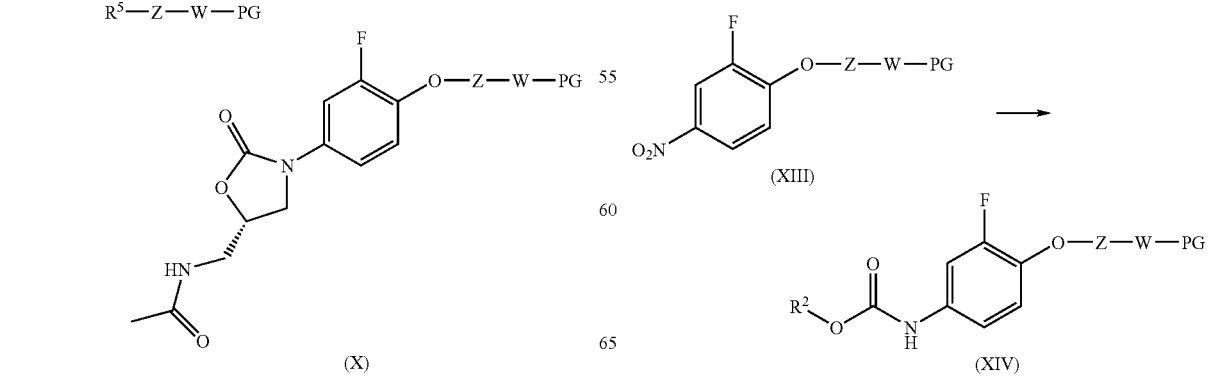

Step 3:
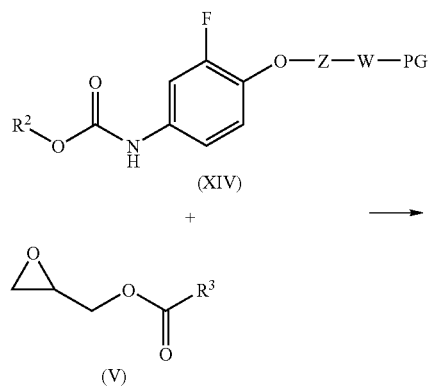
Step 4:
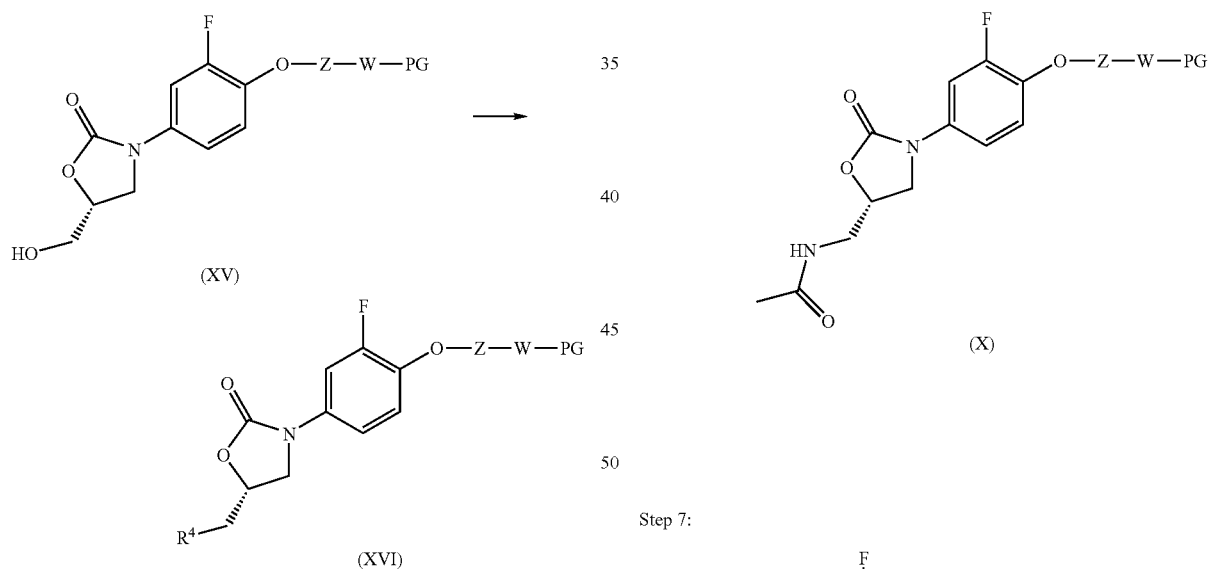
Step 5:
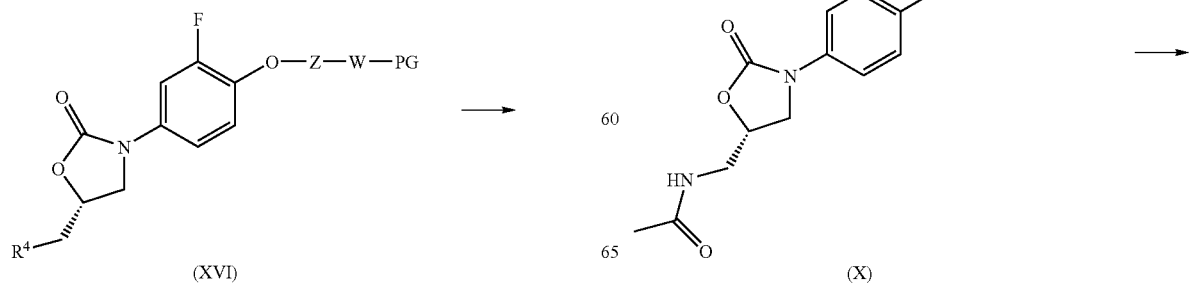
Step 6:
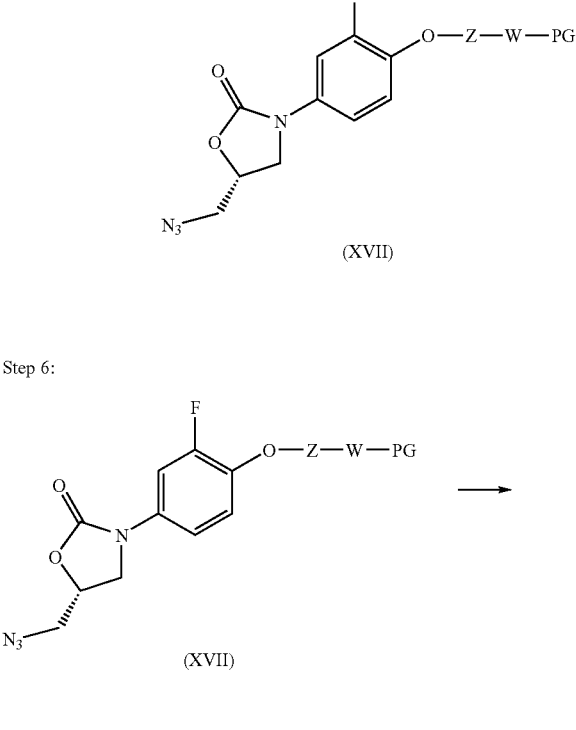
Step 7:

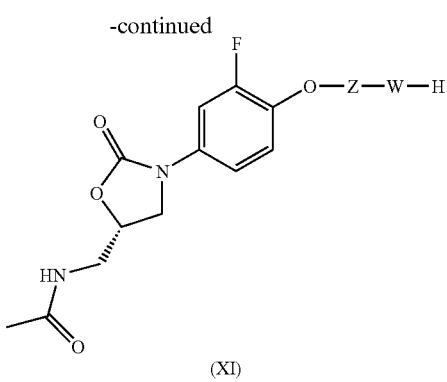

(XI)

When, in that synthesis route, the protecting group PG chosen is the Cbz protecting group, Step 7 is not required, since compound (XI) is obtained directly in Step 6.

In the above formulae:

PG is a protecting group customary per se for amines; especially a benzyloxycarbonyl (Cbz) group;

$R^1$ is an optionally substituted benzyl (for example p-methoxybenzyl) or allyl group;

$R^2$ is a $C_{1-4}$alkyl, an allyl or a benzyl group;

$R^3$ is a $C_{1-4}$alkyl group;

$R^4$ is a mesyloxy, tosyloxy, triflyloxy or texyloxy group or a chlorine, bromine or iodine atom and $R^5$ is a mesyloxy, tosyloxy, triflyloxy or texyloxy group or a chlorine, bromine or iodine atom.

Protecting groups are known to the person skilled in the art and are described, for example, in P. J. Kocienski, Protecting Groups, Georg Thieme Verlag, Stuttgart, 1994 and also in T. W. Greene, P. G. M. Wuts, Protective Groups in Organic Synthesis, John Wiley & Sons, New York, 1999. Common amino-protecting groups are, for example, tert-butoxycarbonyl (Boc), benzyloxycarbonyl (Cbz, Z), benzyl (Bn), benzoyl (Bz), fluorenylmethoxycarbonyl (Fmoc), allyloxycarbonyl (Alloc), trichloroethoxycarbonyl (Troc), acetyl or trifluoroacetyl groups.

In turn, $R^1$ is preferably a benzyl group.

In addition, $R^2$ is preferably a benzyl group.

Furthermore, $R^3$ is preferably an n-propyl group.

In turn, $R^4$ is preferably a mesyloxy group.

In addition, $R^5$ is preferably a mesyloxy group.

Preferred reactions conditions for the first synthesis route are:

For Step 1: $CH_2Cl_2$, potassium hydroxide, room temperature;

For Step 2: hydrogen/Pt/C; then Cbz-Cl, $NaHCO_3$, acetone/water; both at room temperature;

For Step 3: (R)-glycidyl butyrate (V), n-BuLi, −60° C. or LDA, −15° C.;

For Step 4: methylsulphonyl chloride, triethylamine, $CH_2Cl_2$;

For Step 5: $NaN_3$ in DMF, catalytic amounts of $Bu_4NI$, 90° C.;

For Step 6: hydrogen/Pd(OH)$_2$, THF, MeOH; then AcOH, $Ac_2O$; both at room temperature;

For Step 7: dimethylformamide (DMF), sodium hydride, 70° C.;

For Step 8: $H_2$/Pd (OH)$_2$, THF, methanol, room temperature;

Preferred reaction conditions for the second synthesis route are:

For Step 1: Mitsunobu reaction or base (for example NaH), DMF, tosylate of PG-W-Z-OH;

For Step 2: hydrogen/Pt/C; then Cbz-Cl, $NaHCO_3$, acetone/water; both at room temperature or Sn, HCl;

For Step 3: (R)-glycidyl butyrate (V), n-BuLi, −60° C. or LDA, −15° C.;

For Step 4: methylsulphonyl chloride, triethylamine, $CH_2Cl_2$;

For Step 5: $NaN_3$ in DMF, catalytic amounts of $Bu_4NI$, 90° C.;

For Step 6: hydrogen/Pd(OH)$_2$, THF, MeOH; then AcOH, $Ac_2O$; both at room temperature;

There are described in the following Examples the synthesis of compounds of formula (ZP) and the use thereof in the synthesis of compounds of formula (I).

EXAMPLES

Example 1

7-(4-{4-[(5S)-5-(Acetylaminomethyl)-2-oxo-oxazolidin-3-yl]-2-fluorophenoxymethyl}-4-hydroxypiperidin-1-yl)-1-cyclopropyl-6-fluoro-4-oxo-1,4-dihydroquinoline-3-carboxylic acid Step 1: (4-Benzyloxy-3-fluorophenyl)-carbamic acid benzyl ester A mixture of 34.9 g of 1-benzyloxy-2-fluoro-4-nitrobenzene (WO 03 064413) (MW: 247.28, 141 mmol) and 340 mg of platinum (5% on activated carbon) in 350 ml of ethyl acetate was stirred at RT and normal pressure under a hydrogen atmosphere. The course of the reaction was monitored by HPLC and the reaction was terminated after 20 h. The catalyst was filtered off and the filtrate was concentrated to dryness under reduced pressure using a rotary evaporator. The oily residue was dissolved in 500 ml of acetone and 250 ml of a saturated sodium hydrogen carbonate solution and 17.5 g of sodium hydrogen carbonate (MW: 84.01, 208 mmol) were added. The mixture was cooled to 5° C. and 26.08 g of benzyl chloroformate (MW: 170.59, 152 mmol) were added dropwise. The mixture was then stirred for 2 h at RT and the course of the reaction was monitored by TLC (hexane/ethyl acetate 3:1). The acetone was removed under reduced pressure, 500 ml of water were added to the residue, and the solid material was filtered off. The crystals were washed with 500 ml of water and dried.

Yield: 48.05 g, 95.8%. MS: 352.5 (M+H)$^+$, 350.8, (M−H)$^−$. Method: ESI$^+$, ESI$^−$.

Step 2: (5R)-3-(4-Benzyloxy-3-fluorophenyl)-5-hydroxymethyl-oxazolidin-2-one

A stirred solution of 17.5 g of (4-benzyloxy-3-fluorophenyl)-carbamic acid benzyl ester (MW: 351.38, 50 mmol) in 30 ml of dry tetrahydrofuran was cooled to −78° C. using a dry ice/acetone bath. 22.8 ml of a 2.3M n-butyllithium solution in n-hexane (52.5 mmol) were added dropwise and the reaction mixture was stirred at −78° C. for 15 min. 7.92 g of R(−)-glycidyl butyrate (MW: 144.17, 60 mmol) were added and the reaction mixture was heated to RT. The reaction was monitored by HPLC, then quenched with a saturated ammonium chloride solution and diluted with 100 ml of ethyl acetate. The organic phase was washed with 200 ml of water and 200 ml of saturated sodium chloride solution. The organic phase was dried over magnesium sulphate, filtered, and the filtrate was concentrated under reduced pressure. The residue was crystallised from 200 ml of ethyl acetate/hexane (1/1).

The solid material obtained was recrystallised from 150 ml of ethyl acetate/dichloromethane (9/1). The colourless crystals were collected and dried.

Yield: 10.4 g, 65.5%. MS: 318.1 (M+H)$^+$. Method: ESI$^+$.

Step 3: (5S)-5-Azidomethyl-3-(4-benzyloxy-3-fluorophenyl)-oxazolidin-2-one 4.32 g of methanesulphonyl chloride (MW: 114.55, 37.82 mmol) were added at 10° C., with stirring, to a mixture of 10 g of (5R)-3-(4-benzyloxy-3-fluorophenyl)-5-hydroxymethyloxazolidin-2-one (MW: 317.32, 31.51 mmol) and 4.78 g of triethylamine (MW: 101.19, 47.26 mmol) in 300 ml of dichloromethane. The reaction mixture was stirred at RT for 1 h and the course of the reaction was monitored by TLC (ethyl acetate/hexane 1/1). The reaction was quenched with 100 ml of water and the organic phase was washed with 100 ml of saturated sodium chloride solution. The organic phase was dried over magnesium sulphate and filtered, and the filtrate was concentrated under reduced pressure. The residue was dissolved in 100 ml of dimethylformamide and 5.12 g of sodium azide (MW: 65.01, 78.7 mmol) and a catalytic amount of tetrabutylammonium iodide was added. The suspension was stirred overnight at 90° C. The course of the reaction was monitored by HPLC. The dimethylformamide was removed under reduced pressure using a rotary evaporator, the residue was dissolved in 200 ml of dichloromethane and the organic phase was washed in succession with 100 ml of water and 100 ml of saturated sodium chloride solution. The dichloromethane solution was dried over magnesium sulphate and filtered, and the filtrate was concentrated under reduced pressure. The residue was crystallised from 150 ml of ethyl acetate/hexane 1/1. Yield: 10.4 g, 97%. MS: 343.1 (M+H)$^+$. Method: ESI$^+$.

Step 4: N-[(5S)-{3-(3-Fluoro-4-hydroxyphenyl)}-2-oxo-oxazolidin-5-ylmethyl]-acetamide A suspension of 10.4 g of (5S)-5-azidomethyl-3-(4-benzyloxy-3-fluorophenyl)oxazolidin-2-one (MW: 342.33, 30.38 mmol) and 1.5 g of palladium (10% on activated carbon) in 400 ml of a 1:1 methanol:ethyl acetate mixture was stirred for two days at room temperature under a hydrogen atmosphere. The catalyst was filtered off and the filtrate was evaporated under reduced pressure. The residue was dissolved in 100 ml of acetic acid and 3.72 g of acetic anhydride (MW: 102.09, 36.45 mmol) were added. The solvent was evaporated under reduced pressure and the residue was recrystallised from a 1:1 ethyl acetate:hexane mixture. Yield: 6.76 g, 83%. MS: 269.4 (M+H)$^+$, 267.3, (M−H)$^-$. Method: ESI$^+$, ESI$^-$.

Step 5: 4-{4-[(5S)-5-(Acetylaminomethyl)-2-oxo-oxazolidin-3-yl]-2-fluorophenoxymethyl}-4-hydroxypiperidine-1-carboxylic acid benzyl ester A suspension of 22.72 g of 1-oxa-6-aza-spiro[2.5]octane-6-carboxylic acid benzyl ester (WO 98 03507) (MW: 247.29, 92 mmol), 21.45 g of N-[(5S)-{3-(3-fluoro-4-hydroxyphenyl)}-2-oxo-oxazolidin-5-ylmethyl]-acetamide (MW: 268.246, 80 mmol) and 16.58 g of potassium carbonate (MW: 138.20, 120 mmol) in 150 ml of dimethylformamide was stirred at 100° C. for 7 h. The course of the reaction was monitored by TLC (dichloromethane/methanol 9:1). The dimethylformamide was evaporated under reduced pressure and the residue was dissolved in 600 ml of a 9:1 mixture of dichloromethane:methanol. The organic phase was washed with 400 ml of water and 400 ml of saturated sodium chloride solution, dried with magnesium sulphate and filtered and the filtrate was diluted with 250 ml of ethyl acetate. The mixture was concentrated under reduced pressure to a final volume of 400 ml. The mixture was stirred overnight at RT. The crystals were then filtered off and washed in succession with 150 ml of ethyl acetate and 100 ml of pentane. Yield: 31.65 g, 76.7%. MS: 516.8 (M+H)$^+$, Method: ESI$^+$.

Step 6: N-[{(5S)-3-[3-Fluoro-4-(4-hydroxypiperidin-4-yl-methoxy)-phenyl]-2-oxo-oxazolidin-5-ylmethyl}]-acetamide A suspension of 31 g of 4-{4-[(5S)-5-(acetylaminomethyl)-2-oxo-oxazolidin-3-yl]-2-fluorophenoxymethyl}-4-hydroxypiperidin-1-carboxylic acid benzyl ester (MW: 515.54, 60.13 mmol) and 2.5 g of palladium (10% on activated carbon) in 310 ml of methanol and 150 ml of ethyl acetate was stirred for 4 h under a hydrogen atmosphere. The course of the reaction was monitored by TLC (ethyl acetate). The suspension was diluted with 300 ml of methanol, heated to 40° C., and the catalyst was filtered off through a fibreglass filter paper. The filtrate was concentrated to 150 ml, diluted with 300 ml of ethyl acetate and concentrated again to 200 ml. 200 ml of diethyl ether were added and the suspension was cooled, with stirring, to 0° C. The solid material was collected and dried. Yield: 21.6 g, 94.3%. MS: 382.6 (M+H)$^+$, Method: ESI$^+$.

Step 7: 7-(4-{4-[(5S)-5-(Acetylaminomethyl)-2-oxo-oxazolidin-3-yl]-2-fluorophenoxymethyl}-4-hydroxypiperidin-1-yl)-1-cyclo-propyl-6-fluoro-4-oxo-1,4-dihydroquinoline-3-carboxylic acid

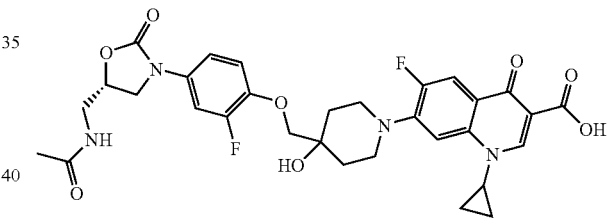

67.81 g of 7-chloro-1-cyclopropyl-6-fluoro-1,4-dihydro-4-oxo-3-quinolinecarboxylic acid/boron diacetate/complex (MW: 410.57, 0.165 mol) were added to a solution of 60 g of N-[{(5S)-3-[3-fluoro-4-(4-hydroxypiperidin-4-ylmethoxy)-phenyl]-2-oxo-oxazolidin-5-ylmethyl}]-acetamide ($C_{18}H_{24}FN_3O_5$, MW: 381.40, 0.157 mol) and 26.87 ml of ethyldiisopropylamine (MW: 129.25, 0.157 mol) in 300 ml of N-methylpyrrolidin-2-one and the mixture was stirred for 5 h at 80° C. The N-methylpyrrolidin-2-one was concentrated under reduced pressure using a rotary evaporator and the residue was dissolved in 300 ml of methanol. Drying agent hydrogen chloride was conveyed through the solution for 30 min. at 10° C. The solution was stirred at RT, a yellow solid being precipitated. The conversion of the boron complex into the free acid was monitored by HPLC. The mixture was diluted with 300 ml of ethyl acetate. The solid material was filtered off and washed with 100 ml of ethyl acetate/methanol (8/2) and 100 ml of ethyl acetate. The yellow solid material was dried, leaving behind 86.4 g of a yellow solid. The solid was dissolved in 200 ml of dimethyl sulphoxide at 40° C. and, with stirring, the yellow solution was poured into 1000 ml of water. The yellow solid was collected, washed with water and dried. Yield: 73 g, 74.5%. MS: 627.8 (M+H)$^+$, 625.8 (M+H)$^-$, Method: ESI$^+$, ESI$^-$.

Example 2
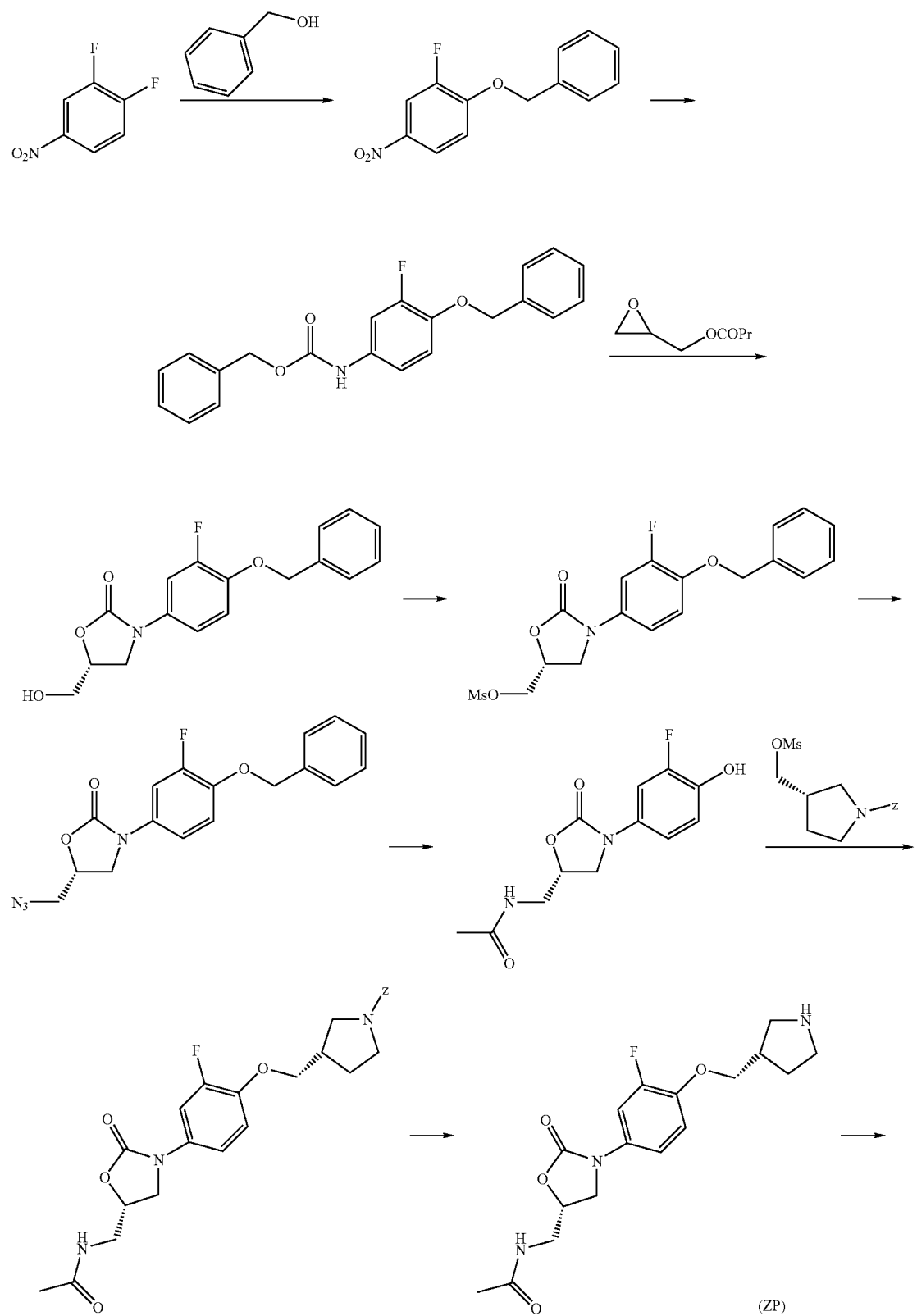

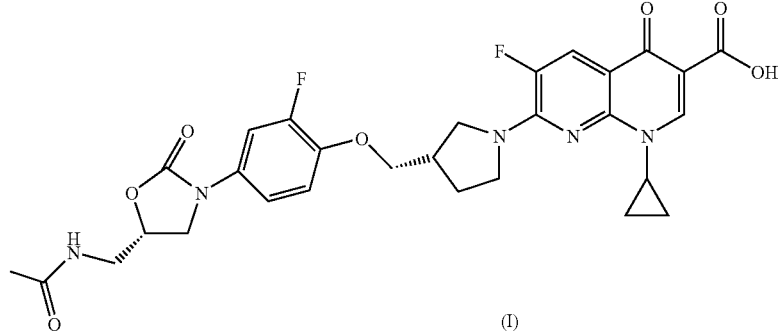

(I)

Reaction conditions:

Step 1: $CH_2Cl_2$, KOH (50%), 3 h, RT; 97%. Step 2: $H_2$, Pt/C, 20 h, RT; then Cbz-Cl, acetone/water, $NaHCO_3$, 12 h, RT, 98%. Step 3: n-BuLi, −60° C., 24 h, 80%. Step 4: MsCl, TEA, $CH_2Cl_2$; 100%. Step 5: $NaN_3$ in DMF, 90° C., cat. $Bu_4NI$, 5 h, 90%. Step 6: $H_2$, $Pd(OH)_2$, THF, MeOH, 24 h, then AcOH, $Ac_2O$, RT, 2 h, 70%. Step 7: DMF, NaH, 70° C., 12 h, 75%. Step 8: $H_2$, $Pd(OH)_2$, MeOH, THF, 24 h, RT, 100%. Step 9: N-methylpyrrolidinone, 1-cyclopropyl-7-chloro-6-fluoro-1,4-dihydro-4-oxo-1,8-naphthydrin-3-carboxylic acid (commercially available), TMSCl, Hünig base or $K_2CO_3$, 80° C., 5 h, 80%.

In none of those Steps is chromatographic separation required.

The following compounds (ZP), or (X), were prepared analogously to the above-described process using suitable starting materials. In the case of compounds containing free OH groups, there were also prepared compounds in which those OH groups are provided with protecting groups (for example acetate, benzoate, MOM ether or isopropylidene).

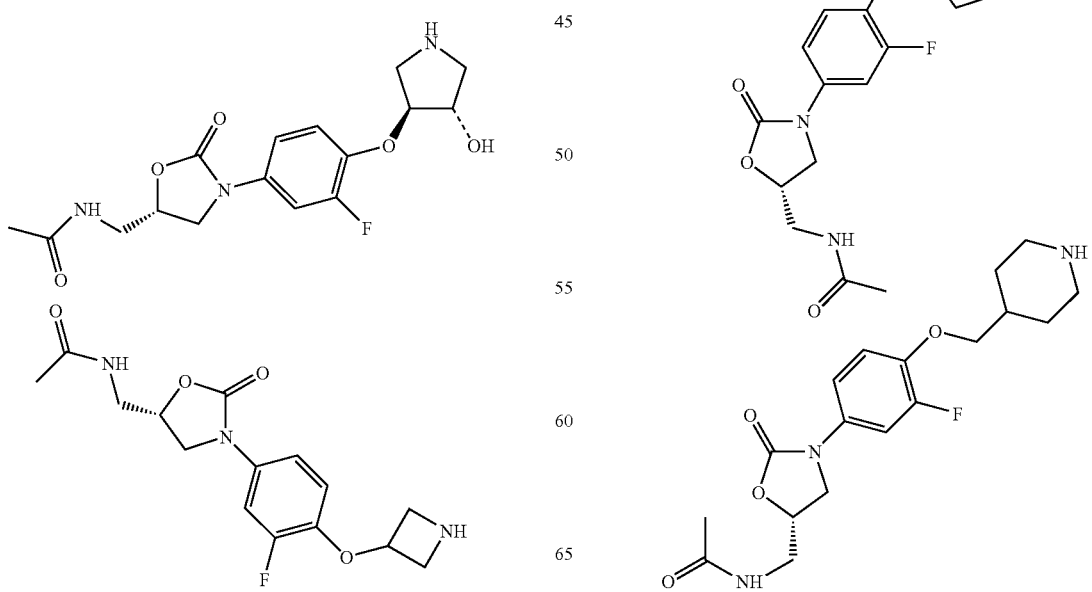

-continued
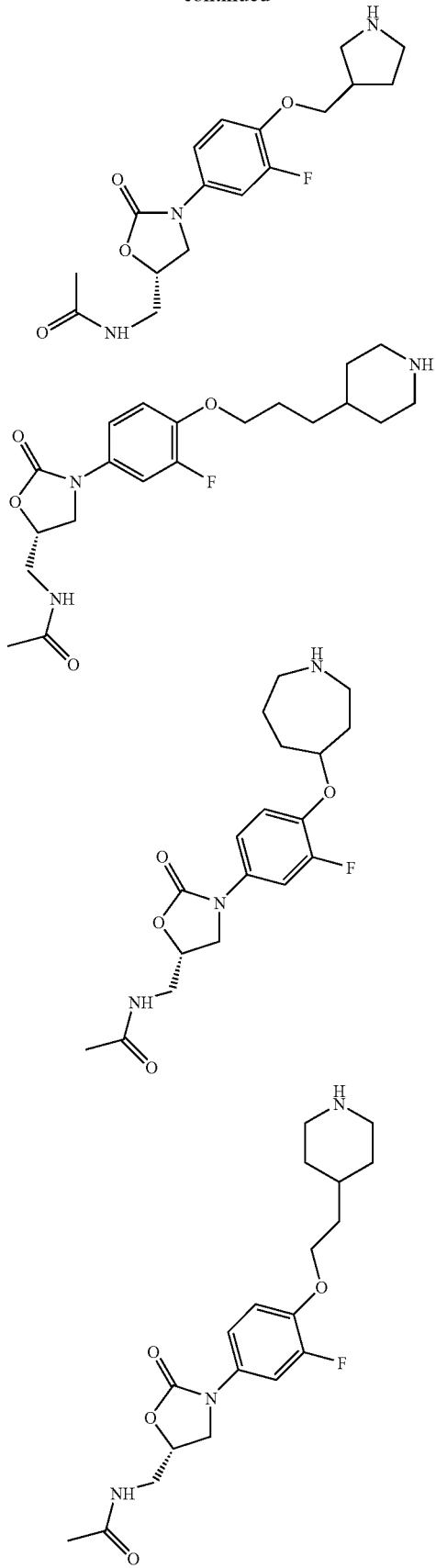
-continued
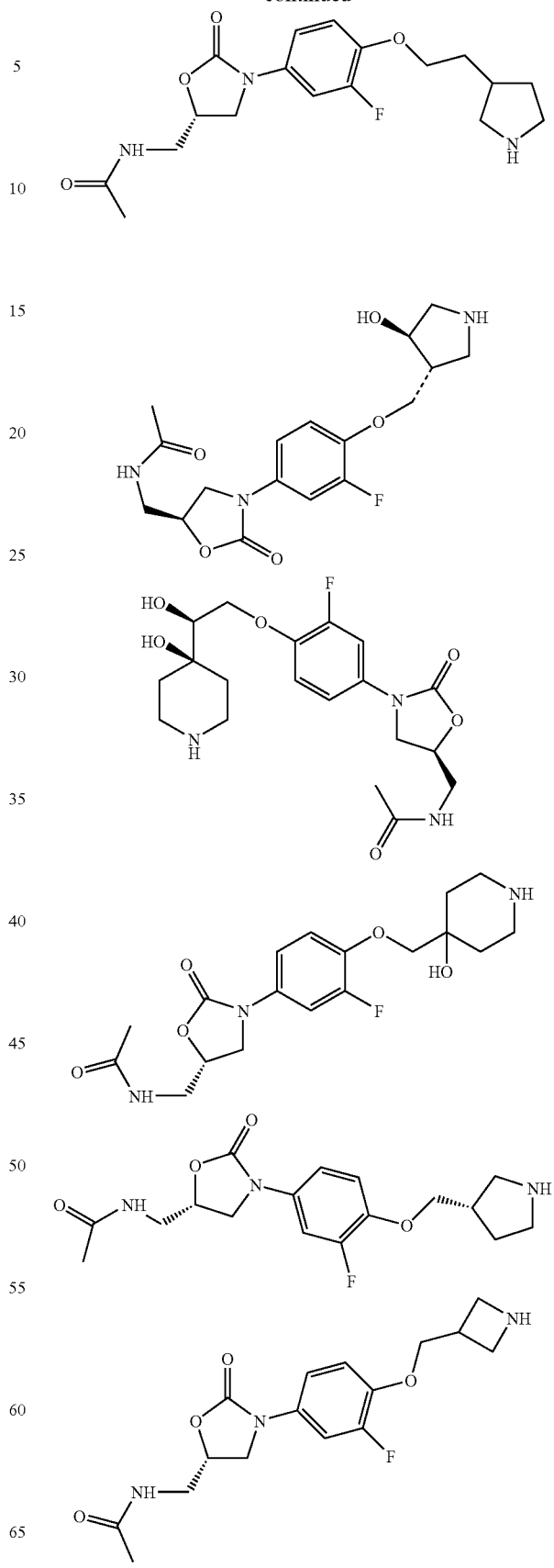

23
-continued
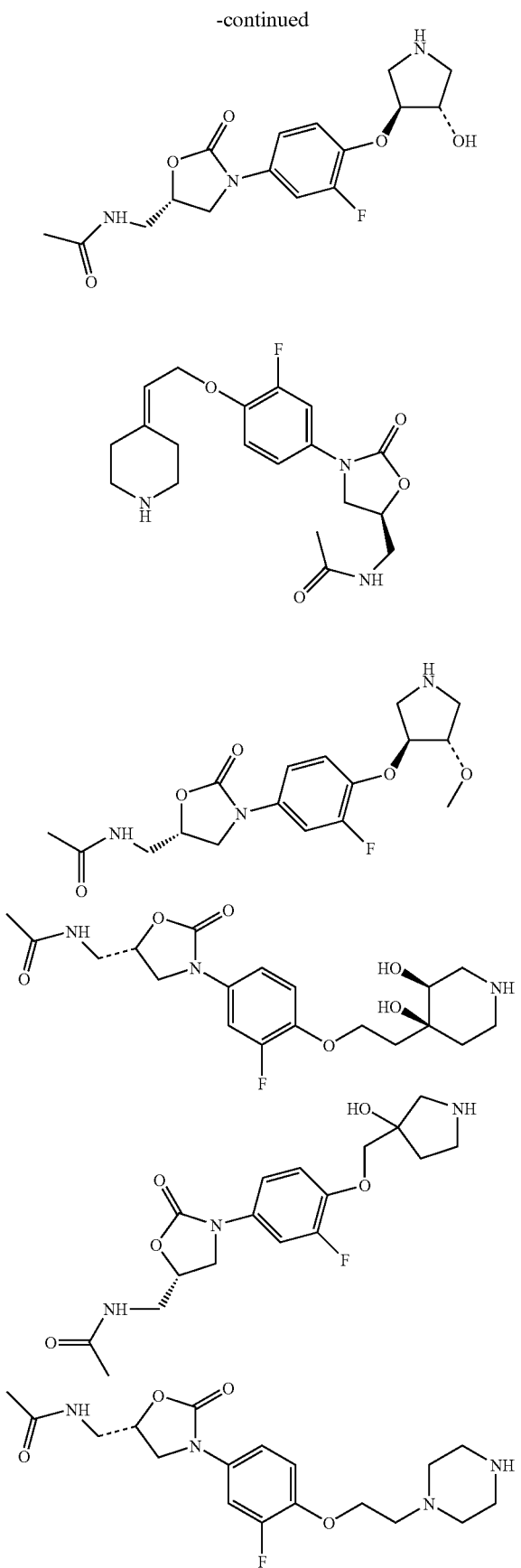
24
-continued
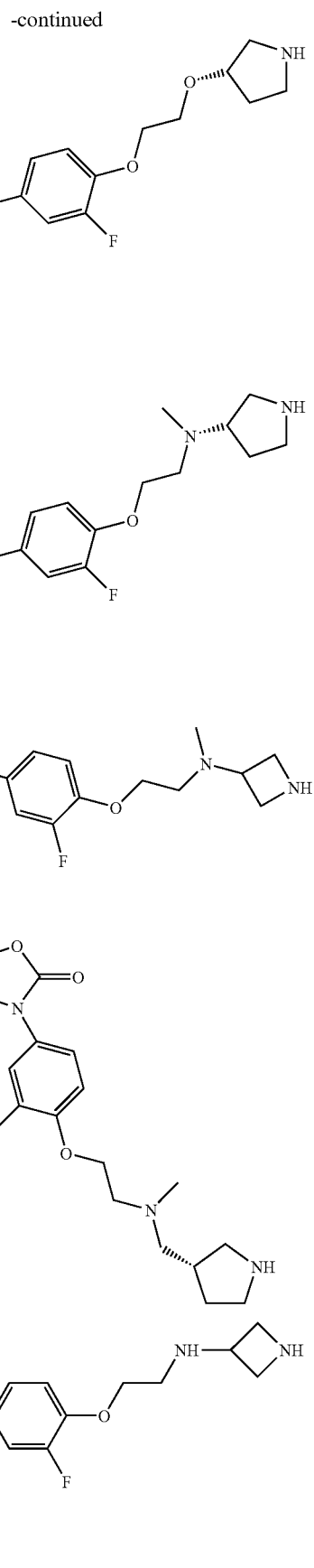

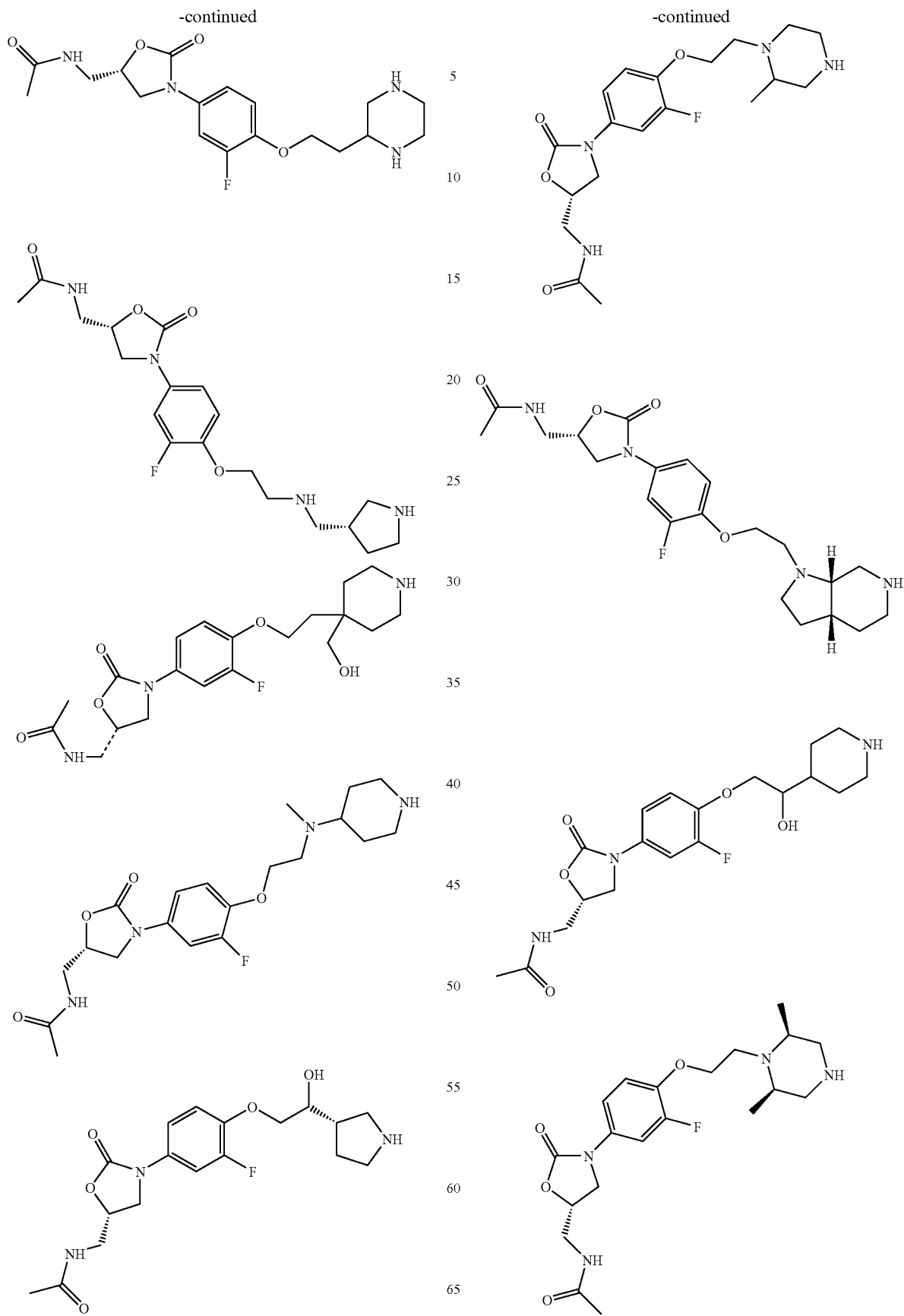

27
-continued
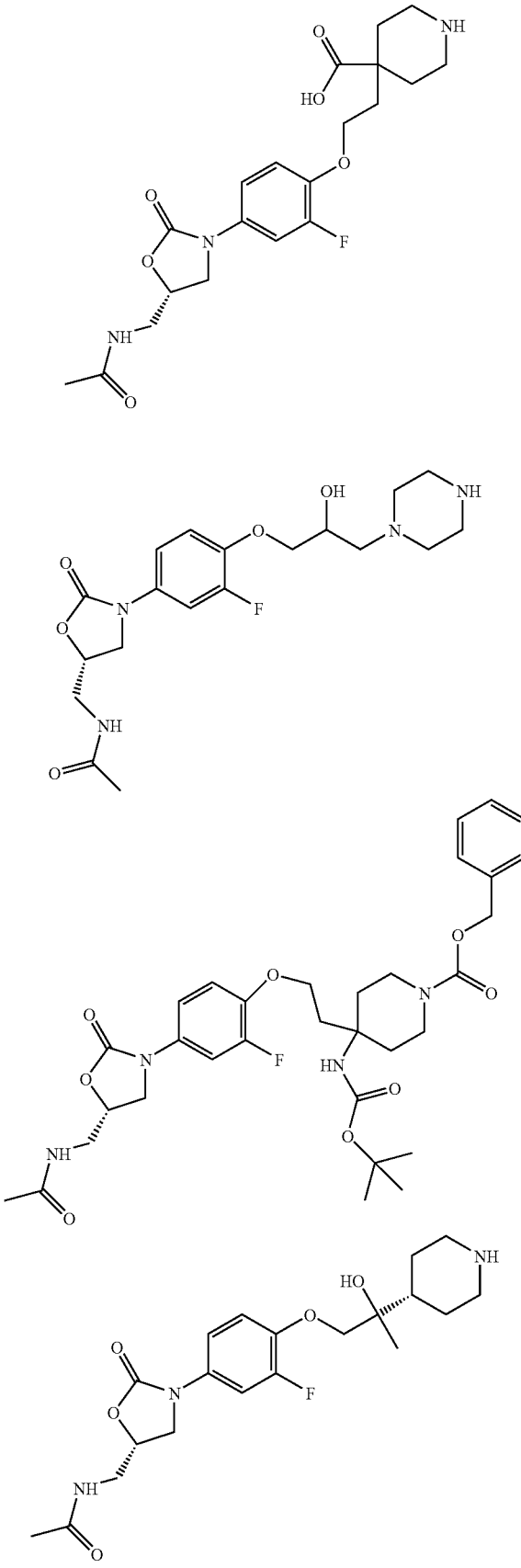
28
-continued
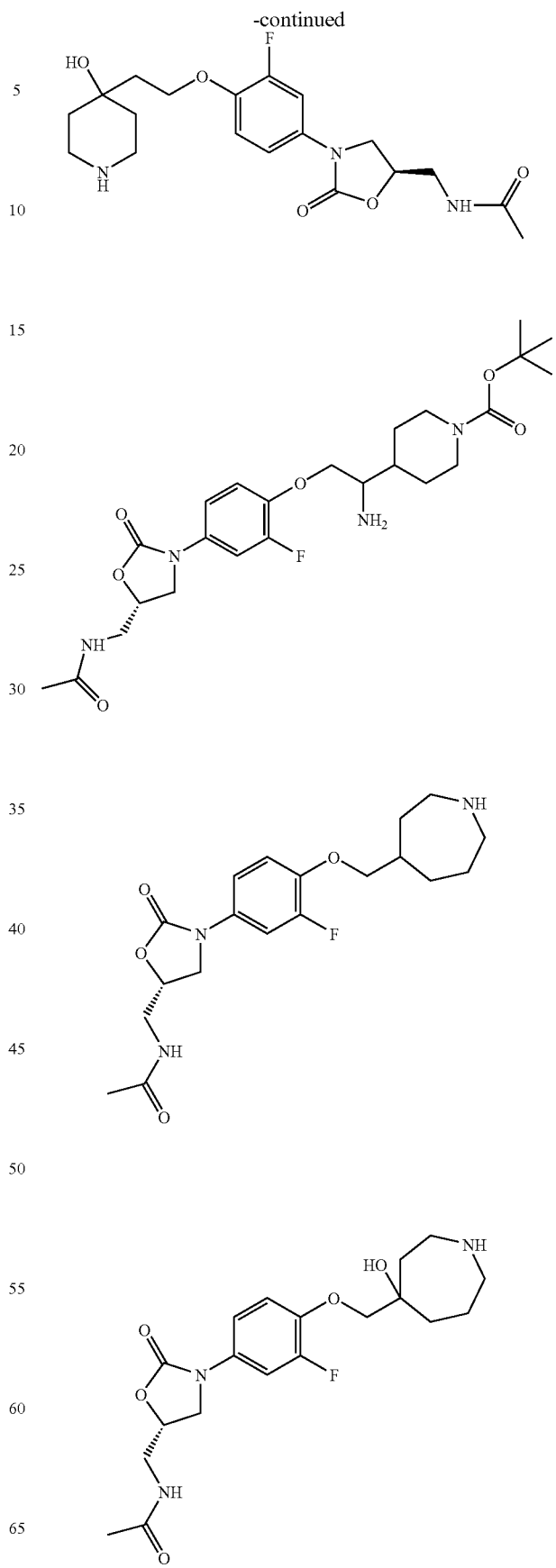

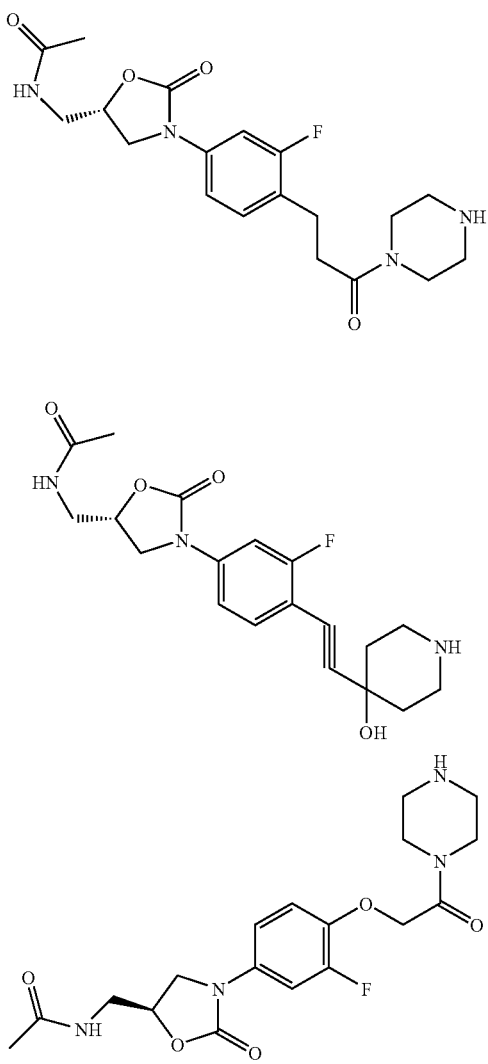

The invention claimed is:

1. A compound of formula (ZP)

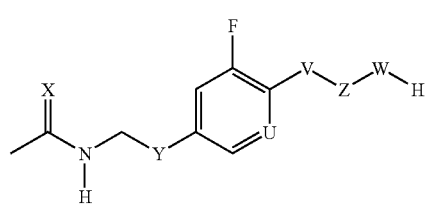

wherein
U is a OH group;
V is an oxygen atom;
Z-W together are a group of formula:

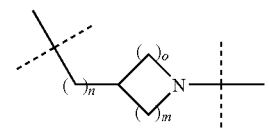

wherein n is 1 or 2, m is 1 or 2 and o is 1 or 2, wherein that group may optionally be substituted by an OH, OPO$_3$H$_2$, OSO$_3$H or a heteroalkyl group carrying at least one OH, NH$_2$, SO$_3$H, PO$_3$H$_2$ or COOH group;
X is an oxygen atom; and
Y is:

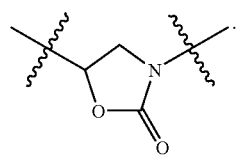

2. A compound of formula (ZP)

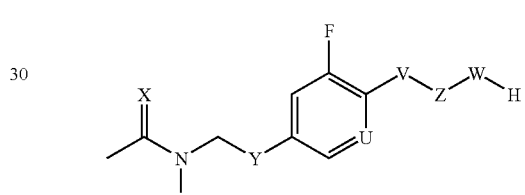

wherein
U is a OH group;
V is an oxygen atom;
W has the following structure:

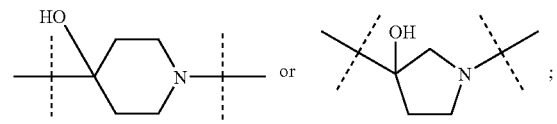

X is an oxygen atom;
Y is:

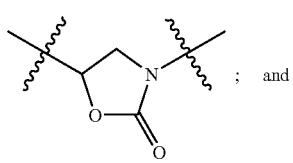
; and

Z is an optionally substituted alkylene, alkenylene, alkynylene, heteroalkylene or heteroaralkylene group.

3. A compound according to claim 2, wherein Z is a C$_{1-4}$ alkylene group.

4. A compound according to claim 2, wherein Z is a CH$_2$ or a CH$_2$CH$_2$ group.

5. A compound of formula (ZP)

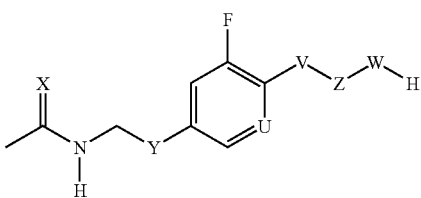
(ZP)

wherein

U is a OH group;

V is an oxygen atom;

W is a heterocycloalkylene group containing a ring having 4, 5, 6 or 7 ring atoms, wherein said heterocycloalkylene group is substituted by an OH group and wherein said heterocycloalkylene group is optionally further substituted;

X is an oxygen atom;
Y is:

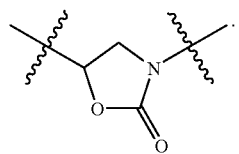

Z is an optionally substituted alkylene, alkenylene, alkynylene, heteroalkylene or heteroaralkylene group.

6. A compound according to claim 5, wherein Z is a $C_{1-4}$ alkylene group.

7. A compound according to claim 5, wherein Z is a $CH_2$ or a $CH_2CH_2$ group.

8. A compound according to claim 5, wherein W has the following structure:

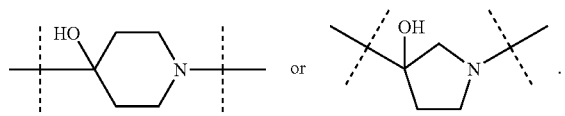

* * * * *

UNITED STATES PATENT AND TRADEMARK OFFICE
CERTIFICATE OF CORRECTION

PATENT NO. : 7,557,214 B2
APPLICATION NO. : 10/570775
DATED : July 7, 2009
INVENTOR(S) : Christian Hubschwerlen et al.

Page 1 of 1

It is certified that error appears in the above-identified patent and that said Letters Patent is hereby corrected as shown below:

Claim 1, column 29, line 64 should read:

-- U is a CH group; -- and

Claim 2, column 30, line 39 should read:

-- U is a CH group; -- and

Claim 5, column 31, line 18 should read:

-- U is a CH group; --

Signed and Sealed this

Tenth Day of November, 2009

David J. Kappos
*Director of the United States Patent and Trademark Office*